United States Patent
Henry et al.

Patent Number: 5,702,394
Date of Patent: Dec. 30, 1997

[54] ASSEMBLY PIECE FOR AN OSTEOSYNTHESIS DEVICE

[75] Inventors: Patrick Henry; Philippe Lapresle, both of Neuilly-sur-Seine; Gilles Missenard, Paris, all of France

[73] Assignee: Stryker Corporation, Kalamazoo, Mich.

[21] Appl. No.: 535,278
[22] PCT Filed: Apr. 19, 1994
[86] PCT No.: PCT/FR94/00437
 § 371 Date: Oct. 19, 1995
 § 102(e) Date: Oct. 19, 1995
[87] PCT Pub. No.: WO94/23661
 PCT Pub. Date: Oct. 27, 1994

[30] Foreign Application Priority Data

Apr. 20, 1993 [FR] France .................. 93 04625

[51] Int. Cl.$^6$ .................................. A61B 17/70
[52] U.S. Cl. .................. 606/61; 606/72; 606/73
[58] Field of Search .................. 606/61, 60, 71, 606/72, 73

[56] References Cited

FOREIGN PATENT DOCUMENTS

| 0509322 | 10/1992 | European Pat. Off. . |
| 0517059 | 12/1992 | European Pat. Off. . |
| 2677874 | 12/1992 | France . |
| 2 033 758 | 5/1980 | United Kingdom ............ A61F 5/04 |

*Primary Examiner*—Michael Buiz
*Assistant Examiner*—Daphja Shai

[57] ABSTRACT

An assembly piece for assembling together two rods ($T_1$, $T_2$) of an osteosynthesis device, in particular for osteosynthesis of the spine. According to the invention, the assembly piece comprises: a body (1) of generally rounded shape having a slot (2) separating the body into two portions (1a, 1b), and two bores (5, 6) on transverse axes (A, B) passing obliquely through the slot, each adapted to receive a respective rod to be assembled; and a clamping screw (3) interconnecting said portions so that tightening the screw locks the two rods in place by clamping them between said portions (1a, 1b).

12 Claims, 3 Drawing Sheets

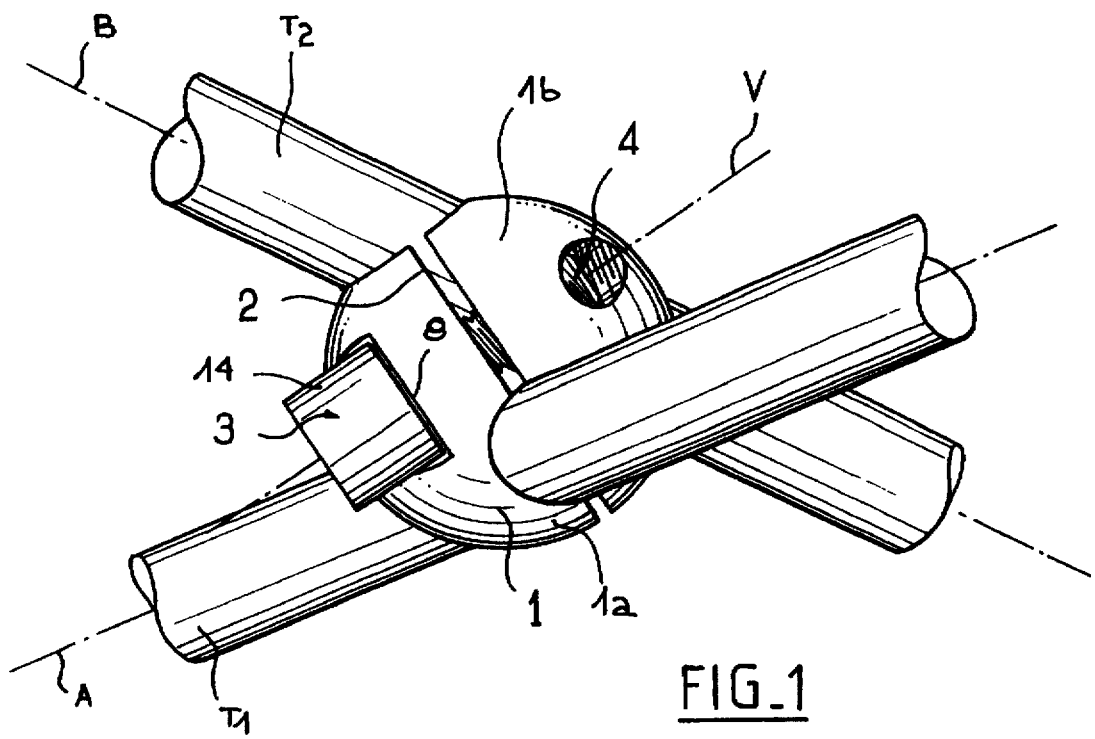
FIG_1
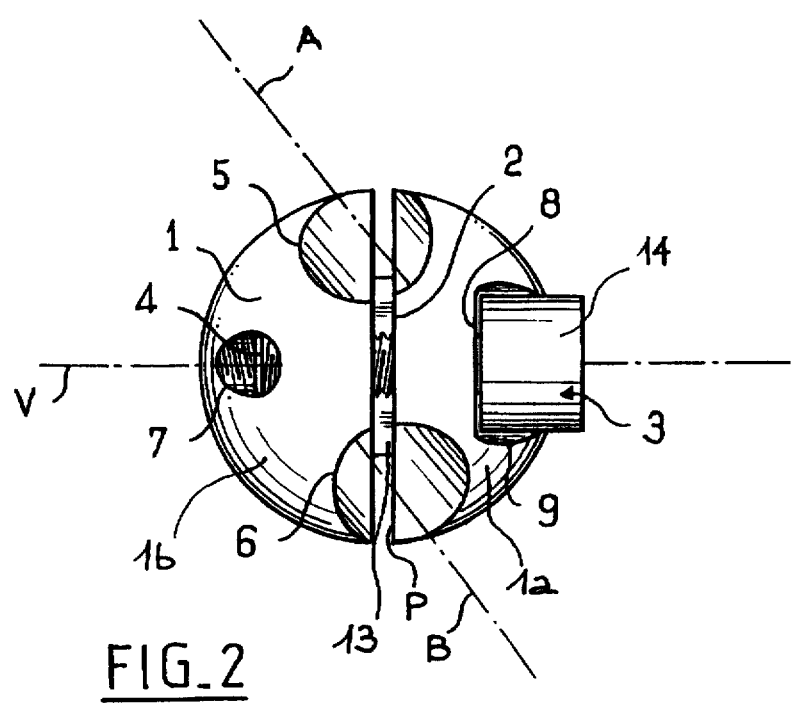
FIG_2

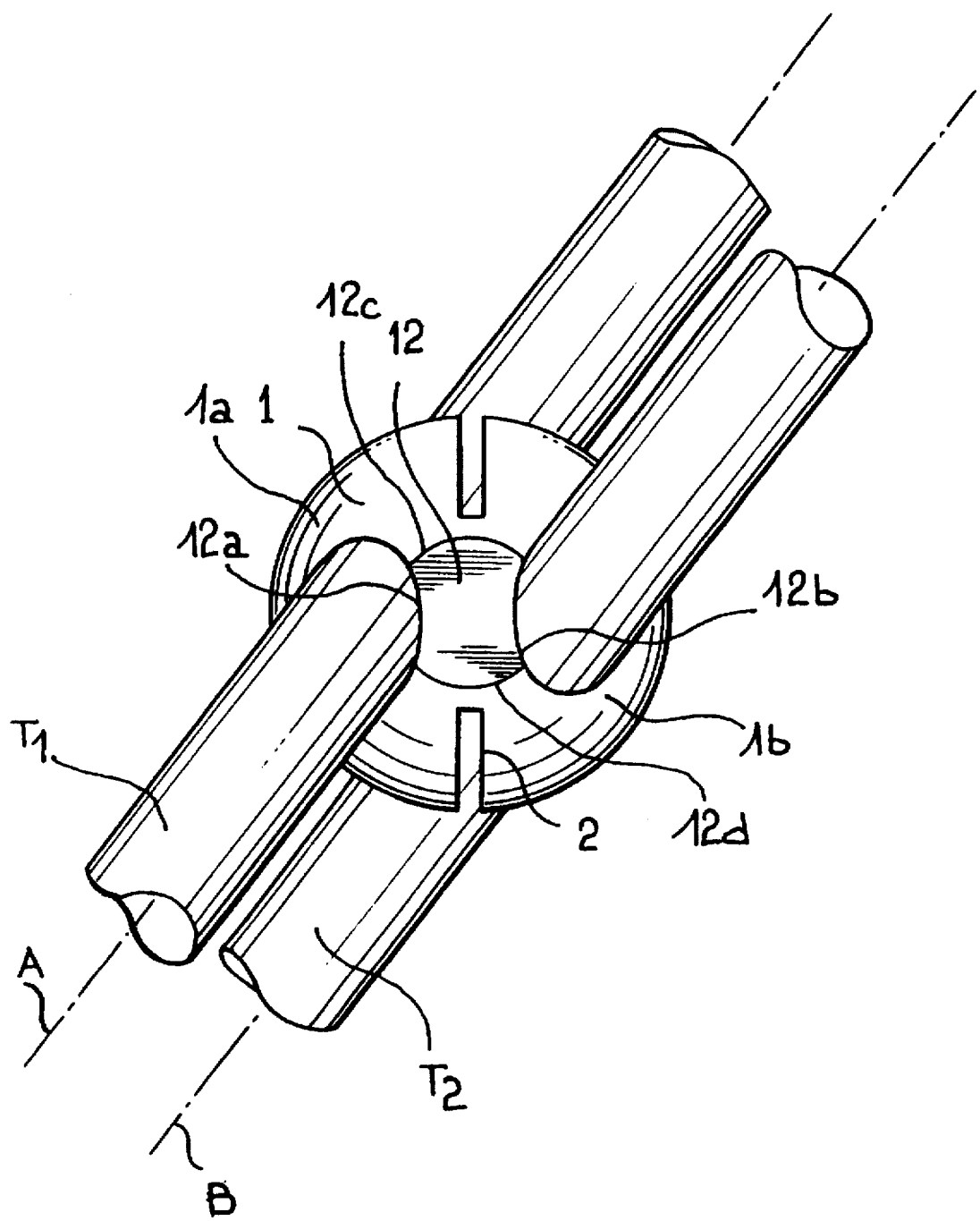
FIG_3

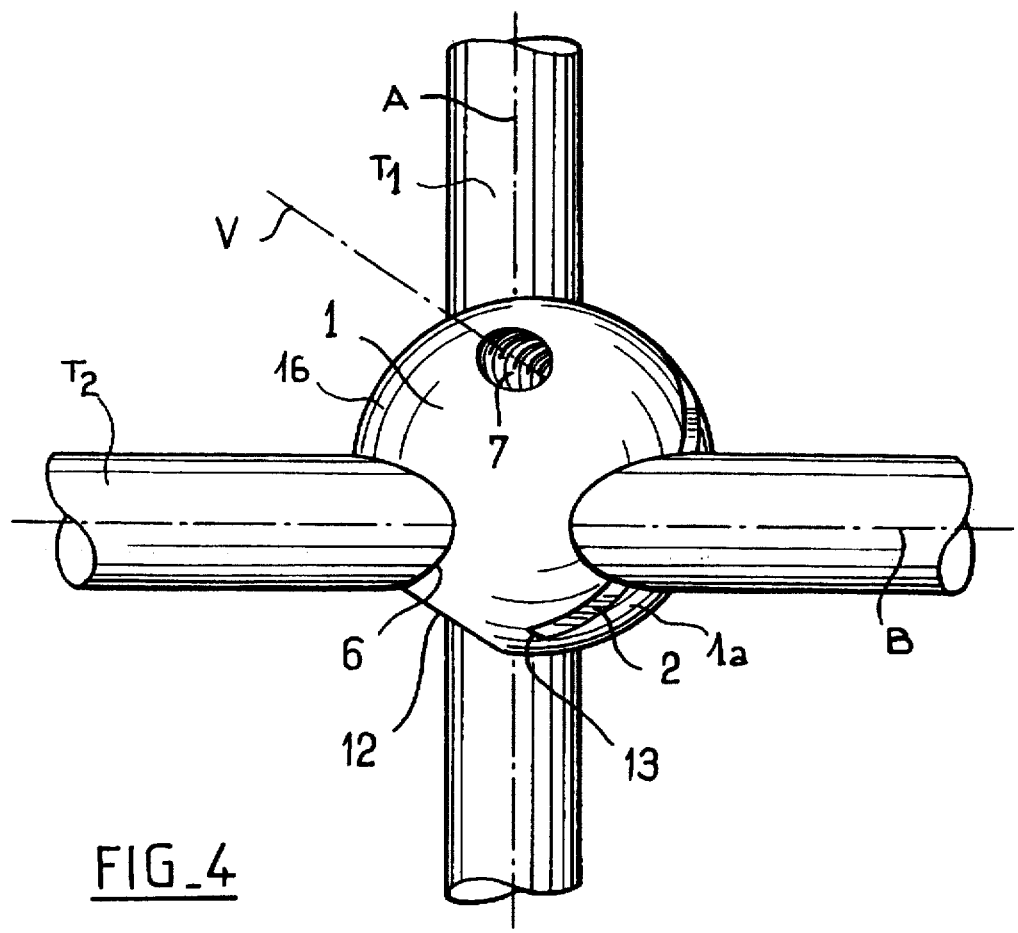
FIG_4
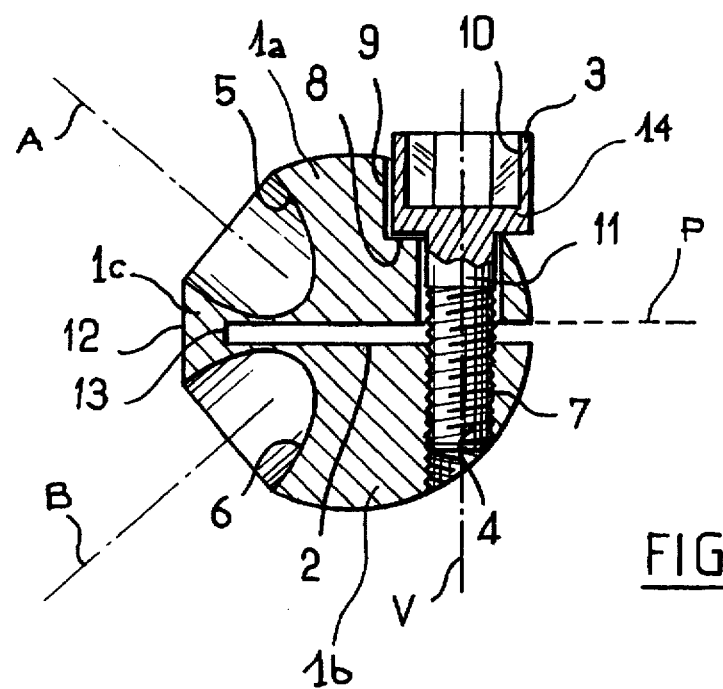
FIG_5

ASSEMBLY PIECE FOR AN OSTEOSYNTHESIS DEVICE

The present invention relates to the field of assembly pieces used in ostheosynthesis, in particular of the spine, and it relates more particularly to a piece for assembling two rods together.

Publication EP-A-0 383 992 discloses an assembly piece used in ostheosynthesis of the spine and serving to interconnect transversely two longitudinal rods that are fixed at several points along their length to the vertebrae. That piece comprises two identical clamp-forming elements for assembling one against the other on a longitudinal rod by means of a threaded rod and two nuts. The assembly pieces are positioned in pairs on the longitudinal rods and the two threaded rods assembling their elements are united by a tapped sleeve for connecting the longitudinal rods together transversely. Installation of the assembly pieces thus makes use of a large number of different elements (nuts, threaded rods, clamp-forming elements, tapped sleeve) which are fiddly to assembly together. In addition, those various elements present projecting angles that run the risk of damaging surrounding tissue.

The present invention seeks to remedy those drawbacks and its object is to provide an improved assembly piece which can be installed easily and quickly and which does not risk damaging surrounding tissue.

According to a first characteristic of the invention, this improved assembly piece comprises:

a body of generally rounded shape having a slot separating the body into two portions, and two bores on transverse axes passing obliquely through the slot, each adapted to receive a respective rod to be assembled; and a clamping screw interconnecting said portions so that tightening the screw locks the two rods in place by clamping them between said portions.

In an advantageous embodiment of the invention, said body is generally spherical in shape, said axes are orthogonal, and said portions are interconnected by a bridge of material defined on the outside by a flat and on the inside by the bottom of the slot, with the slot extending parallel to the flat. Still in an advantageous embodiment of the invention, the screw has a head for coming axially into abutment against a shoulder formed on one of the portions and the screw has a thread for engaging tapping formed in the other portion.

Other characteristics and advantages of the present invention appear on reading the following description of a non-limiting embodiment of the invention, and on examining the accompanying drawings, in which:

FIG. 1 is a perspective view of an assembly piece of the invention with two rods to be assembled together passing through it;

FIG. 2 is a view from above of the piece shown on its own resting via its flat on a plane surface;

FIG. 3 is a view from beneath of the assembly piece with the two rods passing through it;

FIG. 4 is a view taken in a direction orthogonal to the axes of the rods; and

FIG. 5 is a section through the assembly piece on a section plane containing the axis of the screw, and perpendicular to the flat.

The assembly shown in the figures is made from a solid body 1 that is preferably constituted by a titanium alloy. The outside surface of the body 1 is generally in the form of a truncated sphere having a flat 12. The body 1 is split on an equatorial plane P perpendicular to the flat 12 to form a slot 2 separating two generally hemispherical portions 1a and 1b that are connected together by a bridge of material 1c extending between the flat 12 and the bottom 13 of the slot 2. Preferably, as shown, the slot 2 is of constant thickness and its bottom 13 is plane and parallel to the flat 12.

The assembly piece is bored to receive a first rod $T_1$. The bore 5 formed in this way passes through the body 1 along an axis A that intersects both the plane P and the plane tangent to the flat 12 obliquely. The bore 5 opens out at one end in the outside surface of the portion 1a where it intersects the flat 12 on an elliptical arc 12a, and at its other end it opens out on either side of the plane P in the outside surfaces of the portions 1a and 1b.

The body 1 is also bored to receive a second rod $T_2$ for assembly with the first $T_1$. The bore 6 formed in this way passes through the body 1 on an axis B that is orthogonal to the axis A and that intersects obliquely both the plane P and the plane tangential to the flat 12. The bore 6 opens out at one end into the outside surface of the portion 1b where it intersects the flat 12 on an elliptical arc 12b, and at its other end it opens out on either side of the plane P in the outside surfaces of the portions 1a and 1b. The elliptical arcs 12a and 12b are substantially symmetrical to each other about the plane P and their ends are interconnected by opposite substantially equal circular arcs 12c and 12d.

In accordance with the invention, the two portions 1a and 1b are connected together by a clamping screw 3 such that tightening the screw locks the two rods $T_1$ and $T_2$ in place by clamping them between the portions 1a and 1b. As shown, the screw 3 preferably extends along an axis V perpendicular to the plane P, with the axis V being contained in an equatorial plane of the sphere that is perpendicular to the flat 12. The axis V is situated in that one of the two hemispheres defined by an equatorial plane parallel to the flat 12 which is opposite to the hemisphere carrying the flat 12. More precisely, the axis V passes substantially through the middle of the radius extending between the top of said hemisphere and the above-specified equatorial plane.

The portion 1a is bored in stepped manner on the axis V to form a shoulder 8, and the screw 3 has a head 14 that comes axially into abutment against the shoulder 8. The portion 1b is tapped at 7 along the axis V to receive the thread 4 of the screw 3. The thread 4 terminates at a non-threaded cylindrical portion 11 connected to that face of the screw head 14 which comes into abutment against the shoulder 8.

Tightening the screw 3 causes the bridge of material 1c to flex about an axis parallel to the axis V and causes the portions 1a and 1b to move towards each other, thereby locking the rods $T_1$ and $T_2$ in place by clamping between the portions 1a and 1b. The flexibility of the bridge of material 1c depends, in particular, on its thickness, and by having a flat 12 and a slot 2 with a flat bottom 13 parallel to the flat 12, constant thickness is achieved for the bridge of material without any localized points of weakness.

The bores 5 and 6 open out into the slot 2 at an end that is substantially symmetrical on either side of the plane containing the axis V and perpendicular to the flat 12 so the tubes $T_1$ and $T_2$ are clamped with equal force when the screw 3 is tightened, with the screw being tightened by means of a hexagonal key engaged in a socket 10 of complementary shape formed in the end face of the head 14 of the screw.

In the embodiment described, the diameter of the sphere defining the body 1 is about 15 mm. The width of the slot 2 is 1 mm and its depth is about 13 mm. The thickness of the bridge of material 1c as measured between the bottom 13 of the slot and the flat 12 is approximately 1.5 mm. The clamping screw 3 is 15 mm long, the diameter of the thread 4 is 3 mm and it extends over a length of 8 mm. The diameter of the head 14 is 6 mm. The shoulder 8 extends in a plane situated about halfway between the plane P and the plane containing the top of the hemispherical surface defining the portion 1a and parallel to the plane P such that the head 14 of the screw 3 is received for the most part in the circularly cylindrical housing 9 about the axis V and whose bottom constitutes the shoulder 8. The thread 4 projects little from the tapping 7 and the assembly piece does not present projecting angles that run the risk of damaging surrounding tissue.

The assembly piece of the invention is advantageously used for mounting transverse rods between two longitudinal rods that are anchored at several points along their length to the vertebrae by means of implants that are known per se. The assembly pieces are threaded by means of one of their respective bores on the longitudinal rods and they are positioned in pairs thereon for receiving transverse rods through their other respective bores. Advantageously, both bores in a piece have the same diameter so a transverse rod can be implemented using a rod of the same kind as the longitudinal rods. Once the transverse rods have been properly positioned, the screws 3 are tightened.

The present invention is not limited to the embodiment described above. In particular, it is possible to make the assembly piece out of other biologically compatible materials.

What is claimed is:

1. An assembly piece for assembling together two rods of an osteosynthesis device, comprising:
   a body of biologically compatible material and of generally rounded shape, said body having a slot separating said body into two portions and having two bores on transverse axes passing obliquely through said slot, each of said bores being adapted to receive a respective rod to be assembled; and
   a clamping screw interconnecting said portions so that tightening said screw locks the two rods in place by clamping them between said portions.

2. An assembly piece according to claim 1, wherein said body is generally spherical in shape.

3. An assembly piece according to claim 1, wherein said axes are orthogonal.

4. An assembly piece according to claim 1 wherein said portions are interconnected by a bridge of material having a flat outside surface; and wherein a bottom of said slot extends parallel to the plane of said flat outside surface.

5. An assembly piece according to claim 1 wherein said screw includes a screw head for coming into axial abutment against a shoulder formed in one of said portions; and wherein said screw includes a thread for engaging in a tapping formed in the other portion.

6. An assembly piece according to claim 5, wherein said screw extends along an axis perpendicular to said slot.

7. An assembly piece for an osteosynthesis device, comprising:
   a rounded body of biologically compatible material having a slot which separates said body into first and second portions and which extends in a plane and having first and second bores extending along axes which are transverse to one another and which pass through said slot at acute angles to said plane, each of said bores being at least partially located in each of said portions;
   first and second rods received in said first and second bores, respectively, each of said rods directly engaging each of said portions; and
   a clamping screw interconnecting said portions, and locking and clamping said rods in place between said portions upon tightening said screw.

8. An assembly piece according to claim 7, wherein said body is generally spherical in shape.

9. An assembly piece according to claim 7, wherein said axes are orthogonal.

10. An assembly piece according to claim 7 wherein said portions are interconnected by a bridge of material unitarily formed therewith having a flat outside surface; and wherein a bottom of said slot extends parallel to said flat outside surface.

11. An assembly piece according to claim 7 wherein said screw includes a screw head axially abutting a shoulder formed in said first portion; and wherein said screw includes a thread for engaging in a tapping formed in said second portion.

12. An assembly piece according to claim 11, wherein said screw extends along an axis perpendicular to said slot.

* * * * *